(12) United States Patent
Rohrer et al.

(10) Patent No.: US 11,534,541 B2
(45) Date of Patent: Dec. 27, 2022

(54) ADMINISTRATION DEVICE AND METHOD FOR PRODUCING SAME

(71) Applicant: PANTEC AG, Stansstad (CH)

(72) Inventors: Hans-Peter Rohrer, Möhlin (CH); Jürgen Nick, Neuenburg (CH)

(73) Assignee: PANTEC AG, Stansstad (CH)

( * ) Notice: Subject to any disclaimer, the term of this patent is extended or adjusted under 35 U.S.C. 154(b) by 270 days.

(21) Appl. No.: 16/638,232

(22) PCT Filed: Aug. 10, 2018

(86) PCT No.: PCT/EP2018/071815
§ 371 (c)(1),
(2) Date: Feb. 11, 2020

(87) PCT Pub. No.: WO2019/030401
PCT Pub. Date: Feb. 14, 2019

(65) Prior Publication Data
US 2020/0197601 A1 Jun. 25, 2020

(30) Foreign Application Priority Data
Aug. 11, 2017 (CH) .................... 01016/17

(51) Int. Cl.
*A61M 5/14* (2006.01)
*A61M 5/28* (2006.01)
(Continued)

(52) U.S. Cl.
CPC ......... *A61M 5/1409* (2013.01); *A61F 9/0008* (2013.01); *A61J 1/067* (2013.01);
(Continued)

(58) Field of Classification Search
CPC ......... A61J 1/067; A61J 1/2027; A61M 5/282
See application file for complete search history.

(56) References Cited

U.S. PATENT DOCUMENTS

| | | | |
|---|---|---|---|
| 4,346,703 A * | 8/1982 | Dennehey | A61M 5/14 604/905 |
| 5,135,113 A | 8/1992 | Mayer et al. | |

(Continued)

FOREIGN PATENT DOCUMENTS

| | | |
|---|---|---|
| DE | 3122237 A1 | 1/1983 |
| DE | 10009627 A1 | 9/2001 |

(Continued)

OTHER PUBLICATIONS

International Search Report dated Oct. 11, 2018 in corresponding International Application No. PCT/EP2018/071815.
(Continued)

*Primary Examiner* — Laura A Bouchelle
(74) *Attorney, Agent, or Firm* — Medler Ferro Woodhouse & Mills PLLC

(57) ABSTRACT

A delivery device includes a base body having an outlet opening and a chamber for receiving a flowable substance to be administered. The base body, having first and second film portions attached to each other by a connection with a plurality of regions, being configured to discharge the substance through the outlet opening by compressing the chamber. The delivery device further includes a pouring adapter tightly connected to the outlet opening. The plurality of regions of the connection include a more resilient region and a less resilient region that are arranged between the chamber and the outlet opening. When the chamber is compressed to discharge the substance through the outlet opening, the less resilient region is configured to come undone and the more resilient region is configured to remain connected so that the substance can be discharged solely through the outlet opening and the pouring adapter by compressing the chamber.

10 Claims, 2 Drawing Sheets

(51) Int. Cl.
 *A61F 9/00* (2006.01)
 *A61J 1/06* (2006.01)
 *A61J 1/20* (2006.01)

(52) U.S. Cl.
 CPC ............ *A61J 1/2093* (2013.01); *A61M 5/282* (2013.01); *A61M 2207/10* (2013.01)

(56) References Cited

U.S. PATENT DOCUMENTS

| | | | |
|---|---|---|---|
| 5,337,902 | A | 8/1994 | Evans et al. |
| 7,374,040 | B2 * | 5/2008 | Lee .................... A61C 5/60 |
| | | | 206/229 |
| 10,494,157 | B2 * | 12/2019 | Chang .................... B65D 1/08 |
| 2006/0131189 | A1 | 6/2006 | Lee et al. |
| 2009/0026373 | A1 | 1/2009 | Mertens et al. |
| 2014/0346071 | A1 * | 11/2014 | Genosar ................ B65D 25/02 |
| | | | 206/438 |
| 2015/0323452 | A1 | 11/2015 | King et al. |

FOREIGN PATENT DOCUMENTS

| | | |
|---|---|---|
| EP | 1 092 444 A1 | 4/2001 |
| JP | H05-131177 A | 5/1993 |
| JP | 2009-47687 A | 3/2009 |
| JP | 2015-215347 A | 12/2015 |

OTHER PUBLICATIONS

Japanese Office Action issued in corresponding Japanese Patent Application No. 2020-515939 dated May 31, 2022.

* cited by examiner

ADMINISTRATION DEVICE AND METHOD FOR PRODUCING SAME

TECHNICAL FIELD

The invention relates to a delivery device according to the preamble of independent claim 1 and to a method for manufacturing same. Such delivery devices typically comprise a base body, which has an outlet opening and a chamber for receiving a flowable substance to be administered, is composed of a first film portion and of a second film portion that is connected to the first film portion, and is designed to discharge or extract the substance from the delivery device through the outlet opening by compressing the chamber.

BACKGROUND

Nowadays, flowable or liquid substances that are administered in different forms are used for care-related purposes and for the therapeutic treatment of various diseases. For example, such substances are released into body orifices, such as mouth or ears, or injected into a patient's body. For this purpose, the substance is usually applied by means of a specific delivery device that enables targeted application in the specified manner.

For example, care products and medications in the form of eye droplets are often administered to the eyes in order to treat and care for the eyes. It is known to provide the care products or medications in measured portions as a liquid substance in plastic containers for this purpose. For ease of use, such plastic containers often have a beak-shaped outlet opening. During use, the outlet opening is unblocked and positioned on the eye. The liquid substance is then dispensed out of the outlet opening drop by drop by squeezing the container and released into the eye.

Similarly, drugs are also offered that are intended for oral administration. For example, oral vaccinations are applied by means of similar delivery devices.

It is also known to provide substances for subcutaneous, intravenous, or intradermal injection in portioned form in a delivery device. Filled disposable syringes are traditionally used. Alternatively, an intradermal delivery device is described in EP 1 092 444 B1, for example, which comprises a base body made of two layers of a thermoplastic material. The two layers form a reservoir in which a pharmaceutical substance is arranged and an outlet opening that is continuously connected to the reservoir. A connecting piece is incorporated into the outlet opening into which a needle device is inserted. The connecting piece has a sealing membrane that seals the outlet opening. The needle device comprises a needle that is provided both for injection and for piercing the sealing membrane of the connecting piece when the needle device is inserted into the connecting piece. When the needle device is inserted, the substance can be dispensed through the outlet opening and the needle device by compressing the reservoir.

One drawback of the known delivery devices is that the type of administration is usually predetermined. This means that the manufacturing—e.g., the tools used—must usually be adapted for each type of administration. In certain applications, it may also be desirable to select the best type only after the delivery device has been manufactured or even at the time of administration itself. In such cases, several alternative delivery devices must be made available or used. In the case of the aforementioned alternative delivery devices that are intended for injection, the insertion of the needle device can also be problematic. For example, when the needle device is inserted, there is a risk that a portion of the substance will escape immediately, so that the exact dose can no longer be guaranteed. Contamination of the substance to be administered can also occur during the piercing of the sealing membrane. Manufacturing with the connecting piece and its sealing membrane can also be relatively complex.

It is therefore the object of the present invention to propose a device that enables precise, hygienic, and inexpensive administration of medicaments or other sterile substances in different ways, and a method for the efficient and simple manufacturing of such a device.

DESCRIPTION OF THE INVENTION

The object is achieved according to the invention by a delivery device as defined in independent claim 1 and by a manufacturing method as defined in independent claim 16. Advantageous variants of the invention follow from the dependent claims.

The essence of the invention is as follows: A delivery device comprises a base body having an outlet opening and a chamber for receiving a flowable substance to be administered. The base body is made of a first film portion and of a second film portion that is connected to the first film portion. In addition, the base body is embodied such that the substance can be discharged through the outlet opening by compressing the chamber.

The delivery device further comprises a pouring adapter with a connector that is tightly connected to the outlet opening. The connection of the first film portion to the second film portion seals the chamber. The connection also has a plurality of regions that include a more resilient region and a less resilient region that is located between the chamber and the outlet opening. The less resilient region of the connection is designed to come undone when the chamber is compressed in order to discharge the substance through the outlet opening. The more resilient region of the connection is designed to remain connected when the chamber is compressed in order to discharge the substance through the outlet opening. The substance can be discharged or extracted essentially exclusively through the outlet opening and through the connector of the pouring adapter by compressing the chamber.

In connection with the invention, the term "delivery device" can be understood to mean an apparatus that is designed to deliver a controlled, definable amount of the substance in a predetermined form. In particular, it can be a portioned package that is intended for a single or for a few applications.

The substance can particularly be a medicament such as a vaccine or a care product. In order to enable the substance to be administered according to the invention, it is present in a flowable form before application. It can be particularly in liquid form but also gaseous or powdered. The delivery device can be referred to as a dispenser.

The base body can be dimensionally stable, the term "dimensionally stable" referring in this context to a configuration that keeps its shape without external influence. In particular, the base body and the chamber can have a fixed shape during handling of the delivery device, such as during storage, sale, delivery, and removal, for example, until the actual administration. The base body can then be deformed only for the purpose of administration, the chamber being pressed by hand for this purpose, thereby pressing the substance out.

The term "film portion" can refer to a one-part or multi-part structure in connection with the base body. In particular, the first film portion and the second film portion can be two different parts and, in particular, two films that are connected to one another. Or the first and the second film portion can be present in a single piece, i.e., particularly constitute one film. For example, they can be positioned and aligned with one another by means of folds and then connected to one another.

The film portions can be made of a relatively tear-resistant plastic such as a polyvinyl chloride, for example. Alternatively, the film portions can also be made of aluminum or of an aluminum laminate. In principle, any shapable film can be used as a film portion. The material used can be specifically tailored to the respective requirements of the substance or the medicament or the product, such as a barrier effect, light protection, or the like. The plastic of the film portions can be transparent, so that a visual inspection of the contents of the chamber is possible from the outside.

The connection of the first and second film portions is particularly such that the chamber is sealed, more particularly hermetically sealed. This enables the substance to be kept safe and sterile. The more resilient region of the connection can be non-detachable, particularly in this regard, so that it holds when the chamber is compressed and does not come undone, or at least not to a greater extent. It can therefore be permanently tight. It is important that the more resilient region be sufficiently rigid that it can remain connected when the chamber is compressed. The less resilient region of the connection has less resilience, particularly in comparison to the more resilient region. In particular, its resilience is low enough that it detaches sufficiently when the chamber is pressed together so that the substance can penetrate to the pour opening. At the same time, its resilience is high enough that the chamber is tightly sealed.

In connection with the discharging of the substance through the connector of the pouring adapter, the term "essentially exclusively" can refer to the fact that substantially no substance is lost. In particular, the connection can be such that it remains tight in its resilient region and is only loosened in the less resilient region between the chamber and the outlet opening and is therefore permeable.

The delivery device according to the invention can be specifically optimized for the intended application via its pouring adapter. In particular, a fitting part such as a spout, a droplet dispenser, or an injection needle of a desired length, for example, can be mounted on the connector of the pouring adapter in accordance with the desired mode of administration of the substance, such as spraying, dropping, spreading, or injection, for example. As a result, the delivery device makes precise and hygienic administration of medication or other substances possible in a desired manner without tools. The delivery device can be used manually or also via a (semi-)manual device.

The connection of the two film portions and, in particular, the configuration thereof with the regions of different resilience makes it possible to seal the chamber, which breaks open or is opened in a targeted manner. In particular, it enables the chamber to be opened only when the substance is being applied. This ensures the sterility of the substance up to the point of use. It also makes it possible to dispense with additional components such as a needle or the like for opening the chamber. This can be advantageous for preventing contamination and enable a comparatively simple application. Furthermore, it enables a comparatively simple and efficient manufacture of the delivery device. In particular, it can be manufactured in a process such as that known from the manufacturing of conventional blister packs. As a result, the delivery device can also be produced relatively inexpensively. Manufacturing in a sterile environment, which can be particularly advantageous for substances for medical use, is also relatively easy. Furthermore, the deliver device enables a high degree of flexibility in the selection of the materials used. As a result, materials can be readily used that have preferred barrier properties for the substance, for example, or that are preferred in terms of their appearance.

The pouring adapter is preferably made of a resilient material that substantially maintains its shape when the chamber is compressed in order to discharge the substance. As a result, the pouring adapter can be designed in a preferred manner and remain so during the administration of the substance for delivery, particularly including while the chamber is being compressed. This ensures that there is no impairment of the connection of the fitting part during the entire time that the substance is being applied.

The pouring adapter is preferably arranged between the first film portion and the second film portion and securely connected thereto. Such a configuration of the delivery device enables efficient production and reliable application at the same time.

The pouring adapter preferably comprises a sealing portion that is arranged between the first film portion and the second film portion and is securely connected thereto. Such a sealing portion makes an efficient and secure connection to the film portions possible. In particular, it can be designed in such a way—for example with grooves or a similar structure—that the film portions are able to be securely connected.

The connector of the pouring adapter is preferably designed in accordance with a standard or embodied as a Luer lock connector. Such a standardized connector enables various fitting parts to be mounted on the delivery device in a simple and efficient manner. This makes it possible for these parts to be connected in a known manner, which can keep the handling of the delivery device comparatively simple. Such connectors can also be used to ensure that the connection is secure.

The chamber is preferably formed in the first film portion. The second film portion is preferably planar. In this context, the term "planar" can refer to an even or flat shape. The first film portion is preferably composed of a plastic that is produced in a deep-drawing process or of an aluminum that is produced in a deep-drawing process. The second film portion can also be composed of such a plastic or aluminum. The aluminum can be aluminum laminate in particular as well. Such a configuration of the film portions enables the delivery device to be manufactured efficiently, particularly in a manner analogous to the manufacturing of known blister packs.

The first film portion is preferably embodied as a first film and the second film portion as a second film. The second film can be made in such a way that it is not inherently dimensionally stable. It can be a cover foil such as that known from conventional blister packs.

The first film portion or the second film portion or the first film portion and the second film portion can be provided with an antiseptic layer. Such an antiseptic layer enables the substance in the delivery device to be kept sterile without the need for costly additional measures. This can be preferred particularly where medical substances are involved.

For the connection, the first and the second film portion can be glued, mechanically hooked, sealed, or welded to one another. The connection preferably comprises sealed seams. The sealing or welding can be carried out by means of a thermal process or by means of ultrasound, for example. In particular, the sealed seams of the connection are preferably produced by thermal sealing.

The more resilient region of the connection preferably has sealed seams of greater resilience, and the less resilient regions of the connection preferably have sealed seams of lesser resilience. In this way, the more resilient and less resilient regions of the connection can be efficiently produced in a desired quality.

The delivery device can also have a plurality of chambers. For example, substances can be arranged in the several chambers and mixed together before administration.

To achieve this, the delivery device is preferably configured as follows: The base body has an additional chamber for receiving an additional substance component. The connection seals the additional chamber off. The less resilient region of the connection is arranged between the additional chamber and the chamber. The less resilient region of the connection is designed to come loose when the additional chamber is compressed in order to discharge the substance from the additional chamber. The more resilient region of the connection is designed to remain connected when the additional chamber is compressed in order to discharge the substance component. The substance component can be transferred essentially exclusively from the additional chamber into the chamber by compressing the additional chamber.

In this context, the term "substance component" can be understood to mean a substance which, together with a substance that is arranged in the chamber, forms the substance that is to be ultimately discharged. For example, the substance component can be solvent that is transferred from the additional chamber into the chamber and reconstitute a lyophilisate there to form the substance. Such an arrangement can make it possible for the substance that is to be applied to be prepared or mixed only shortly before application and to be hermetically separated beforehand. Among other things, this can be advantageous for purposes of durability.

Alternatively, the substance component can also be an additional substance that is dispensed together with the substance or separately therefrom. This makes it possible to efficiently apply a plurality of substances.

Another aspect of the invention relates to a method for manufacturing a delivery device, particularly as described above. The method comprises the following steps: (i) manufacturing a first film portion that is produced in a deep-drawing process; (ii) forming a chamber in the first film portion; (iii) manufacturing a second film portion that is preferably produced in a deep-drawing process; (iv) sterilizing the first film portion and the second film portion; (v) positioning a pouring adapter with a connector; (vi) filling the chamber with a sterile, flowable substance that is to be administered under sterile conditions; (vii) creating a connection of the first film portion to the second film portion under sterile conditions, so that the pouring adapter is tightly connected to the base body, and the connection has a plurality of regions, including a more resilient region and a less resilient region that is arranged between the chamber and the outlet opening.

The above steps of the method according to the invention can also be carried out in a different order than as indicated, (i)-(vii). A plurality of steps can also be carried out together. For example, the forming of the chamber in the first film portion can occur together with the manufacturing thereof in a single step combination. Or the two film portions can be produced in one step, which can be expedient particularly if the first and second film portions are to be formed in one piece. The manufacturing of the film portions in steps (i) and (iii) can correspond to a manufacturing of the first film portion or the second film portion in a deep-drawing process. The chamber can be formed by cold forming, which can be advantageous in the case of a first film portion that is made of aluminum or aluminum laminate, for example, or thermoforming, which can be advantageous in the case of a first film portion that is made of plastic, for example. The deep-drawing process can therefore include cold forming and/or thermoforming.

Since the steps of filling the chamber with the sterile, flowable substance that is to be administered and closing the chamber are carried out by securely connecting the first film portion to the second film portion under sterile conditions, the method according to the invention makes it possible that no additional sterilization is necessary. In particular, the need for the execution of subsequent sterilization measures such as gamma irradiation can be avoided. This can prevent the substance from being adversely affected by these measures. For example, this enables certain substances with biological active substances to even be provided in the first place in a delivery device of the type according to the invention. This is typically not possible, because the additional sterilization mentioned damages the biological active substances. What is more, the method according to the invention enables efficient manufacturing with relatively few method steps, for example in a so-called inline process.

Moreover, with the method according to the invention, the delivery device described above or a similar delivery device can be manufactured efficiently, for example in a manner analogous that used for conventional blister packs. This enables the effects and advantages as described above in connection with the delivery device and its preferred embodiments to be implemented efficiently.

A pouring adapter is preferably arranged adjacent to the filled chamber, the pouring adapter being securely connected to the first film portion and the second film portion when the chamber is closed. In terms of timing, the term "when the chamber is closed" can refer to a connection both during the closing of the chamber and before or after the closing of the chamber. This enables an especially simple and efficient implementation of the pouring adapter in the delivery device.

The less resilient region of the connection is also preferably designed to come undone when the chamber for discharging the substance through the outlet opening is compressed, and the more resilient region of the connection is designed to remain connected when the chamber for discharging the substance through the outlet opening is pressed, so that the substance can be discharged essentially exclusively through the outlet opening and through the connector of the pouring adapter by compressing the chamber.

Some preferred embodiments of the method according to the invention are described below which can be provided in order to achieve the effects and advantages of the above-described corresponding embodiments of the delivery device according to the invention and/or to achieve additional effects and advantages.

The pouring adapter can be made of a resilient material that substantially maintains its shape when the chamber is compressed in order to discharge the substance through the outlet opening.

When the chamber is closed, the pouring adapter can be arranged between the first film portion and the second film portion and securely connected thereto by securely connecting the first film portion to the second film portion. To achieve this, the pouring adapter preferably comprises a sealing portion that is arranged between the first film portion and the second film portion and is securely connected thereto. In terms of timing, the pouting adapter is preferably connected to the first and/or second film portion before the chamber is closed.

Preferably, the pouring adapter is attached to the first film portion during the positioning and before the filling of the chamber.

The first film portion can be composed of a plastic that is produced in a deep-drawing process or of an aluminum that is produced in a deep-drawing process. The second film portion can be planar.

The first film portion can be embodied as a first film and the second film portion as a second film, the first film being securely connected to the second film. The second film portion can be made from an aluminum foil.

The first film portion or the second film portion or the first film portion and the second film portion can be provided with an antiseptic layer.

The connection of the first film portion to the second film portion is preferably established under sterile conditions by thermal sealing. Such a connection step can be carried out quickly and cost-effectively, and a secure connection can be established. The connection is preferably established by sealed seams, preferably by means of thermal sealing. The more resilient region of the connection is formed by means of sealed seams of greater resilience, and the less resilient regions of the connection are formed by sealed seams of lesser resilience. The different sealed seams can be produced by different process parameters such as pressure, temperature, or duration.

The connector of the pouring adapter is preferably designed in accordance with a standard or embodied as a Luer lock connector.

BRIEF DESCRIPTION OF THE DRAWINGS

Additional advantageous embodiments of the invention follow from the following description of an exemplary embodiment of the invention with reference to the schematic drawing. In particular, the delivery device according to the invention is described in greater detail below with reference to the accompanying drawing using the exemplary embodiment. In the drawing.

MANNER(S) OF CARRYING OUT THE INVENTION

Figure 1:
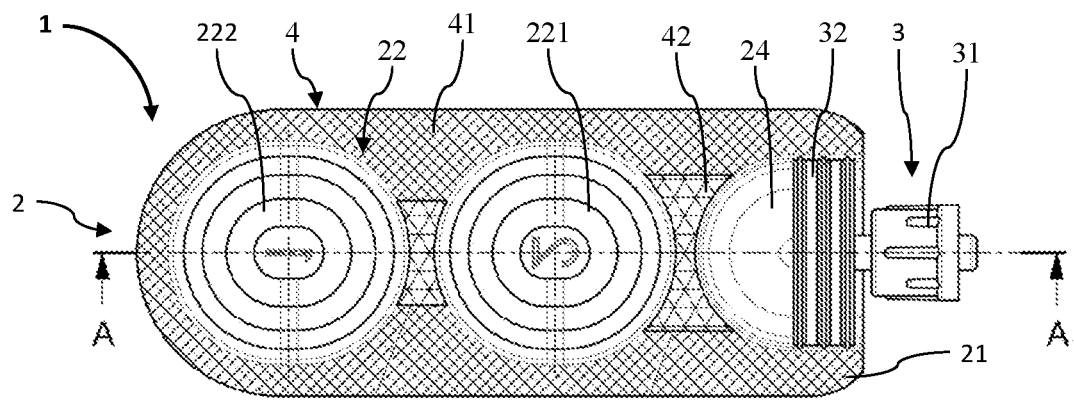
FIG. 1 shows a schematic top view of a dispenser as an exemplary embodiment of a delivery device according to the invention.

Certain expressions are used in the following description for practical reasons and are not to be understood as limiting. The words "right," "left," "below," and "above" indicate directions in the drawing to which reference is being made. The expressions "inward," "outward," "below," "above," "left," "right," or the like are used to describe the arrangement of designated parts relative to one another, the movement of designated parts relative to one another, and the directions toward or away from the geometric center of the invention and of named parts thereof as illustrated in the figures. This relative spatial information also includes positions and orientations that are different from those shown in the figures. For example, if a part shown in the figures is turned over, elements or features that are described as "below" are then "above." The terminology includes the words expressly mentioned above, derivatives thereof, and words of similar meaning.

In order to avoid repetitions in the figures and the associated description of the different aspects and exemplary embodiments, certain features are to be understood as being common for different aspects and exemplary embodiments. The omission of an aspect in the description or a figure does not suggest that this aspect is missing in the associated exemplary embodiment. Rather, such omission can be conducive for clarity and prevent repetition. In this context, the following statement applies to the entire description that follows: If reference symbols are contained in a figure for the sake of clarity in the drawing but not mentioned in the passage of the description directly associated therewith, reference is made to the explanation thereof in the preceding description of the figures. Furthermore, if reference symbols are also mentioned in the passage of the description directly associated with a figure which are not contained in the associated figure, reference is made to the preceding and following figures. Similar reference symbols in two or more figures stand for similar or identical elements.

FIG. 1 shows a dispenser 1 as an exemplary embodiment of a delivery device according to the invention. The dispenser 1 is particularly embodied as a portioned package. It comprises a dimensionally stable, manually deformable base body 2, which has a first film 21 as the first film portion. Two chambers 22 and an outlet opening 24 are formed in the first film 21. A portion of a lyophilized active pharmaceutical ingredient is arranged in a right first chamber 221 and a liquid solvent in the left second chamber 222. The outlet opening 24 comprises an outlet chamber that is formed on the right edge of the base body 2. The basic body 2 has an approximately rectangular basic shape when viewed from above. The first film 21 is composed of an aluminum laminate that is manufactured in a deep-drawing process.

The dispenser 1 further comprises a pouring adapter 3 with a Luer lock connector 31 and a structured sealing portion 32. It is securely connected to the base body 2 at its sealing portion 32, so that the Luer lock connector protrudes from one of the shorter transverse sides of the base body 2.

Figure 2:
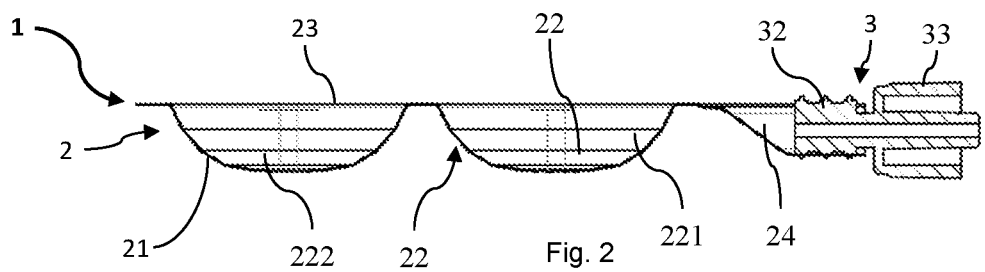
FIG. 2 shows a side view of the dispenser from FIG. 1.

In FIG. 2, the dispenser 1 is shown from the side. In addition to the first film 21, the base body 2 is produced from a second film 23 as a second film portion. The second film 23 is made of aluminum laminate and has a flat design. The chambers 22 are embodied as downwardly extending bulges in the first film 21. The second film 23 is located on the first film 21 and is securely and tightly connected thereto by means of a connection 4 that is formed from sealed seams and shown in FIG. 1. The chambers 22 are thus hermetically sealed.

The connection 4 comprises a more resilient region 41 and a less resilient region 42. The more resilient region 41 is arranged particularly between the chambers 22 and the periphery of the base body 2. The less resilient region 42 of the connection 4 is arranged between the first chamber 221 and the outlet chamber of the outlet opening 24 and between the first chamber 221 and the second chamber 222.

As can be seen in FIG. 2, the pouring adapter 3 has a horizontal channel. The channel forms an outlet opening of the dispenser 1 that transitions into a fitting part (not shown in the figures) that is mounted on the Luer lock connector.

Figure 3:
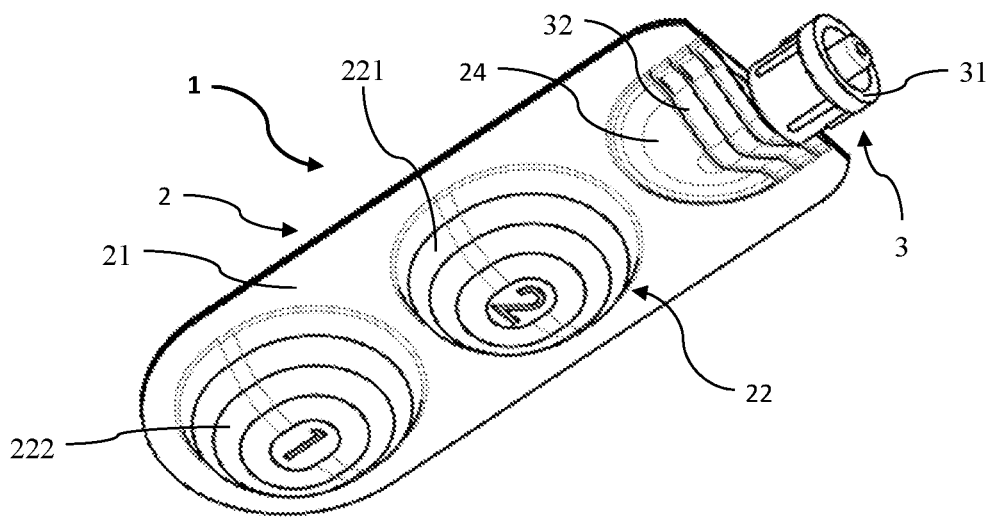
FIG. 3 shows a first perspective view of one of the surfaces of the dispenser of FIG. 1.

FIG. 3 shows a perspective view of dispenser 1 from the first film 21. The sealing portion 32 of the pouring adapter 3 has a quasi-triangular shape in the front view, the Luer lock connector 31 projecting centrally therefrom. The sealing portion 32 is arranged between the first film 21 and the second film 23 and is securely and tightly connected thereto.

Figure 4:
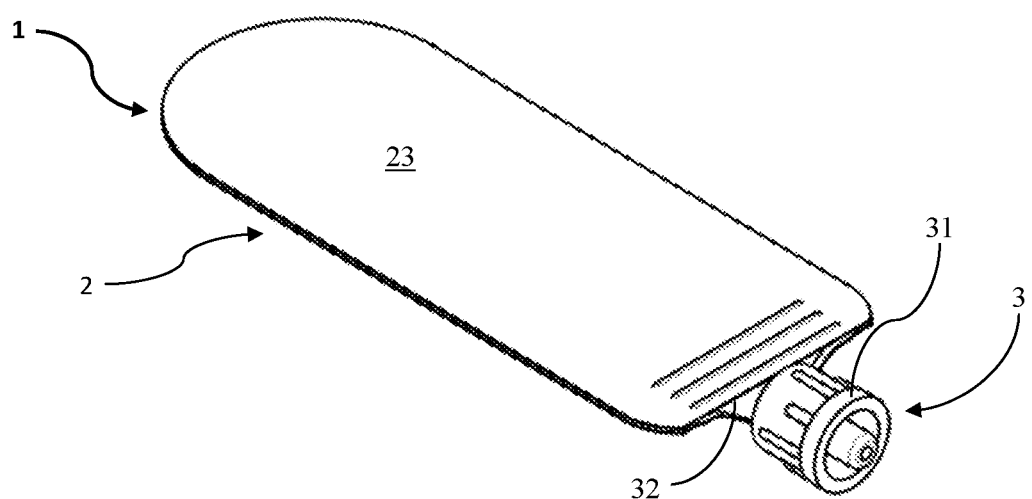
FIG. 4 shows a second perspective view of the other, oppositely situated one of the surfaces of the dispenser from FIG. 1.

As can be seen in FIG. 4, the second film 23 forms a completely flat or planar surface of the base body 2 of the dispenser 1. The spout 3 is made of a resilient material that substantially maintains its shape when the chambers 22 are compressed in order to discharge the substance—e.g., the medicament—through the pouring adapter 3.

When using the dispenser 1, a fitting part such as an injection needle, for example, is mounted on the Luer lock connector 31. In a first step, the second chamber 222, which is provided with a numeral one for illustration, is then compressed. Due to the overpressure produced in this way in the second chamber 222, the less resilient region 42 between the first chamber 221 and the second chamber 222 is released, so that a passage is created between these two chambers. The solvent is conveyed into the first chamber 221, where it reconstitutes the lyophilized drug to the substance to be administered. The injection needle is then applied to a patient and the first chamber 221 is compressed. As a result, an overpressure is produced in the first chamber 221 by means of which the less resilient region 42 between first chamber 221 and outlet opening 24 is released, so that a passage is created between these two chambers. The substance is then discharged through the outlet opening 24, the pouring adapter 3, and the injection needle and injected. In order to prevent the substance from flowing back from the first chamber 221 into the second chamber 222, either the second chamber 222 is held together while the first chamber is compressed, or the base body 2 is folded over between the first chamber 221 and the second chamber 222.

The dispenser 1 can be manufactured as follows in a manner analogous to that used for a conventional blister pack. The first film 21 is manufactured in a deep-drawing process, the chambers 22 being formed in the first film portion, for example through thermoforming. The second film 23 is manufactured or prepared. The first films 21 and the second film 23 are sterilized, and the chambers 22 are filled with the associated substance components under sterile conditions. The prefabricated pouring adapter 3 is arranged adjacent to the filled chamber 22. The chamber 22 is then closed by securely connecting the first film 21 to the second film 23 under sterile conditions, while the sealing portion 32 of the spout 3 is securely and tightly connected to the films 21, 23.

Although the invention is illustrated and described in detail by means of the figures and the associated description, this illustration and this detailed description are to be understood as illustrative and exemplary and not as restrictive of the invention. In order not to transfigure the invention, well known structures and techniques cannot be shown and described in detail in certain cases. As will readily be understood, those skilled in the art can make changes and modifications without departing from the scope of the claims that follow. In particular, the present invention covers additional exemplary embodiments with any combination of features that may differ from the combinations of features explicitly described.

The present disclosure also includes embodiments with any combination of features mentioned or shown above or below for various embodiments. It also includes individual features in the figures, even if they are shown there in connection with other features and/or are not mentioned above or below. In addition, the alternative embodiments and individual alternatives for the features thereof that are described in the figures and the description can be excluded from the subject matter of the invention and/or from the disclosed objects. The disclosure includes embodiments that only include the features described in the claims or in the exemplary embodiments and also those that include additional other features.

Furthermore, the term "comprise" and derivatives thereof do not exclude other elements or steps. Likewise, the indefinite article "a" or "an" and derivatives thereof do not exclude a multitude. The functions of several features listed in the claims can be fulfilled by a unit or a step. The terms "substantially," "about," "approximately," and the like in connection with a characteristic or a value also cover precisely that characteristic and that value. The terms "about" and "approximately" in connection with a given numerical value or range can refer to a value or range that lies within 20%, within 10%, within 5%, or within 2% of the given value or range. None of reference symbols in the claims are to be understood as limiting the scope of the claims.

What is claimed is:

1. A delivery device, comprising:
    a base body defining
        a chamber for receiving a flowable substance to be administered, and
        an outlet opening, the outlet opening comprising an outlet chamber for receiving the flowable substance from the chamber,
        wherein the base body is composed of a first film portion and a second film portion, the first and second film portions being attached to each other by a connection, the base body being configured to discharge or extract the substance through the outlet chamber and the outlet opening by compressing the chamber;
    a pouring adapter composed of a resilient material that substantially maintains its shape when the chamber is compressed in order to discharge the substance, the pouring adapter having a channel extending from a first end to a second end thereof, the pouring adapter including
        a sealing portion having a quasi-triangular shape in a front view, the sealing portion being arranged between the first film portion and the second film portion to be securely connected thereto, within the outlet opening of the base body, such that the channel of the pouring adapter is in fluid communication with the outlet chamber of the base body, and
        a connector portion extending from the sealing portion, the connector portion being configured to be connected to a fitting part such that the channel of the pouring adapter is in fluid communication with the fitting part; and
    a fitting part comprising one of a spout, a droplet dispenser and an injection needle of a desired length mounted on the connector portion of the pouring adapter in accordance with a desired mode of administration of the substance from the delivery device, wherein the desired mode of administration of the substance comprises one of spraying, dropping, spreading and injection,
    wherein the connection of the first film portion to the second film portion seals the chamber and has a plurality of regions that include a more resilient region and a less resilient region, the less resilient region being located between the chamber and the outlet chamber, and wherein, when the chamber is compressed, the more resilient region is designed to remain connected and the less resilient region is designed to come undone in order to discharge the substance essentially exclusively through the outlet chamber, through the channel of the pouring adapter and finally through the fitting part.

2. The delivery device of claim 1, wherein the connector of the pouring adapter is designed in accordance with a standard or embodied as a Luer lock connector.

3. The delivery device of claim 1, wherein the chamber and the outlet chamber of the outlet opening are formed in the first film portion.

4. The delivery device of claim 3, wherein the second film portion is planar.

5. The delivery device of claim 1, wherein the first film portion is composed of a plastic that is produced in a deep-drawing process or of an aluminum that is produced in a deep-drawing process.

6. The delivery device of claim 1, wherein the first film portion is embodied as a first film and the second film portion is embodied as a second film.

7. The delivery device of claim 1, wherein the second film portion is composed of an aluminum foil.

8. The delivery device of claim 1, wherein the first film portion or the second film portion is or the first film portion and the second film portion are provided with an antiseptic layer.

9. The delivery device of claim 1, wherein the connection comprises sealed seams, wherein the sealed seams of the connection are produced by thermal sealing, and wherein the more resilient region of the connection has sealed seams of greater resilience and the less resilient region of the connection has sealed seams of lesser resilience.

10. The delivery device of claim 1, wherein the base body has an additional chamber for receiving an additional substance component, the connection seals the additional chamber off, wherein an additional less resilient region of the connection is arranged between the additional chamber and the chamber, the additional less resilient region of the connection is designed to come undone when the additional chamber is compressed in order to discharge the substance component from the additional chamber into the chamber, and the more resilient region of the connection is designed to remain connected when the additional chamber is compressed in order to discharge the substance component, so that the substance component can be transferred essentially exclusively from the additional chamber into the chamber by compressing the additional chamber.

\* \* \* \* \*